United States Patent [19]

Kaufman et al.

[11] Patent Number: 5,004,803

[45] Date of Patent: Apr. 2, 1991

[54] PRODUCTION OF PROCOAGULANT PROTEINS

[75] Inventors: Randal J. Kaufman, Boston; Debra Pittman, Arlington, both of Mass.

[73] Assignee: Genetics Institute, Inc., Cambridge, Mass.

[21] Appl. No.: 270,882

[22] Filed: Nov. 14, 1988

[51] Int. Cl.$^5$ .................. C07K 13/00; C12N 5/06; C07H 15/12; C11N 15/64
[52] U.S. Cl. .................................... 530/383; 530/381; 435/69.6; 435/240.1; 435/240.2; 435/320.1; 514/12; 536/27
[58] Field of Search ............... 530/381, 383; 435/69.6, 435/240.1, 320, 240.2; 514/12; 536/27

[56] References Cited

PUBLICATIONS

Kane, W. et al. (1988) *Blood* 71(3), 539–555.

*Primary Examiner*—Margaret Moskowitz
*Assistant Examiner*—R. Keith Baker
*Attorney, Agent, or Firm*—Bruce M. Eisen; Luann Cserr; David Berstein

[57] ABSTRACT

Hybrid procoagulant proteins are disclosed which contain peptide sequences of human blood coagulation factors V and VIII. DNA molecules encoding these proteins and materials and methods for expressing them are also disclosed. Preferably, peptide sequence in the B domain of Factor VIII is replaced with peptide sequence derived from human Factor V.

5 Claims, No Drawings

PRODUCTION OF PROCOAGULANT PROTEINS

Human factor VIII:C (FVIII) is an increasingly well known protein cofactor in the coagulation cascade. DNA sequences encoding FVIII are known [see e.g., Toole et al, 1984, Nature 312:312–317; Wood et al, 1984, Nature 312:330–337; Vehar et al, 1984, Nature 312:337–342], as are methods for expressing such DNAs to produce recombinant FVIII [see e.g. WO 87/04187, WO 88/08035 and WO 88/03558]. Procoagulant-active FVIII analogs and DNA sequences encoding them have also been reported [see e.g. WO 86/06101 and WO 87/07144]. Generally, such analogs are modified such that part or all of the B domain are missing and/or specific amino acid positions are modified, for example, such that normally protease-labile sites are resistant to proteolysis, e.g. by thrombin or activated Protein C. Other analogs include modification at one or more lysine and/or tyrosine residues.

For reasons that have still not been determined with certainty, recombinant FVIII expression proceeds at relatively low levels. Various methods have been developed which contribute to enhancing the otherwise low expression level of FVIII and analogs thereof, including expression in the presence of von Willebrand Factor (vWF) or analogs thereof [see e.g., WO 87/04187 and WO 88/08035], expression of FVIII in cells expressing lower levels of an endogenous endoplasmic reticulum protein known as BiP [see e.g., WO 88/03558], and deletion within the B domain of FVIII and analogs thereof [see e.g., WO 86/06101].

Factor V (FV) is another high molecular weight glycoprotein cofactor involved in the coagulation cascade. A gene encoding human FV has been cloned, sequenced and expressed in mammalian cells [see e.g., Jenny et al, 1987, Proc Natl Acad Sci USA 84:4846–4850].

While different from one another in sequence, FVIII and FV share common organizational characteristics, both being expressed by DNAs encoding three "A" domains, a "B" domain and two "C" domains, as depicted schematically below:

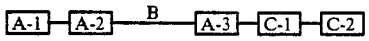

Also, highly acidic peptide regions precede A-2 and A-3 in FVIII.

It has also been surprisingly found that the B domain is dispensable for the procoagulant activity of FVIII, and that active procoagulant protein can be expressed and secreted by expression of a FVIII-encoding DNA in which the nucleotide region encoding part or all of the B domain is lacking. Not only is active protein produced and secreted, it accumulates in the media at higher levels than when expressed by the full-length DNA.

The reduced level of active procoagulant FVIII protein in the media has been attributed, at least in part to several factors [see e.g. WO 87/04187, WO 88/08035 and WO 88/03558].

This invention provides new hybrid DNAs encoding hybrid procoagulant proteins which may be produced by recombinant techniques in higher yield and/or in more homogeneous form than recombinant human FVIII. Furthermore, the proteins of this invention may be more stable procoagulants or may give rise to more stable activated species, and may not be inhibited by antibodies to native FVIII, and thus may be preferred in the treatment of bleeding disorders in patients with such antibodies.

The hybrid proteins of this invention encompass procoagulant- or coagulant-active FVIII proteins which contain in place of part or all of one or more domains the corresponding polypeptide portions of FV. DNAs encoding the hybrid proteins of this invention are thus defined as DNAs which encode a protein having procoagulant or coagulant activity, as measured by conventional assays as described in greater detail below, and which are capable of hybridizing under stringent conditions to a cDNA encoding FVIII, preferably human FVIII, and to a cDNA encoding FV, preferably human FV. The DNA may be further modified, e.g. at one or more sites encoding proteolytic cleavage sites, sulfation sites, etc. as disclosed in WO 87/07144, and/or by deletion within the region encoding the B-domain. The DNA may further be modified as described in WO 87/07144 but at corresponding FV sites.

It is contemplated that the hybrid FVIII-FV proteins encoded by these chimeric genes and which contain part or all of the FV B domain in place of the corresponding FVIII region will be capable of expression at levels higher than typically obtained with wild-type FVIII. Indeed, that appears to be true in cases evaluated thus far (see e.g. Table II). Furthermore, it is contemplated that the proteins produced may be obtainable as a one-chain protein (e.g. where specific proteolytic cleavage sites are additionally modified) or as a two-chain protein. In the latter case, it is contemplated that the protein may be obtained as an approximately 90/80 kD complex upon proteolytic excision the FV or FVIII B-domain or as a complex of an approximately 80 kD protein fragment with a heavy chain ranging from approximately 90 kD up to about 200 kD. In all cases, it is contemplated that the protein obtained will retain procoagulant activity in conventional coagulation assays, as described in greater detail below.

DNA SEQUENCES OF THIS INVENTION

One aspect of this invention provides a DNA sequence encoding a polypeptide sequence substantially the same as human FVIII or variants thereof modified as is now known in the art or disclosed in various patent applications, except within the region encoding one or more domains such as the B-domain, i.e., between amino acid positions 740 and 1649, with numbering beginning with the mature N-terminus, Ala-1. Within those regions, the DNA sequence comprises a nucleotide sequence encoding a peptide sequence the same or substantially the same as that of human FV. It should be understood that the remainder of the DNA sequence may encode native human FVIII or may comprise additional modification to delete part of the polypeptide sequence, as disclosed e.g. in WO 86/06101 or WO 87/07144, and/or modification at one or more specific sites as disclosed e.g. in WO 87/07144, which also disclose exemplary oligonucleotides and methods for effecting such additional modification.

Variant DNA in accordance with this invention also include allelic variations, i.e. variations in sequence due to natural variability from individual to individual, or with other codon substitutions or deletions which still retain Factor VIII:c-type procoagulant activity.

Thus this invention encompasses DNA sequences encoding a procoagulant protein which sequences are capable of hybridizing under stringent conditions to the wildtype human FVIII-encoding cDNA insert in pSP64-VIII, discussed below, so long as the DNA sequence is modified within the region encoding the B domain as described herein. The DNA sequences of this invention are also capable of hybridizing under stringent conditions to a human FV cDNA, such as pMT2-V (ATCC No. 40515) discussed below.

PRODUCTION OF DNA SEQUENCES OF THIS INVENTION

All variant DNAs of this invention may be prepared by modifying DNA sequences encoding human FVIII. The variant DNA sequences may be produced by conventional site-directed mutagenesis of DNA sequences encoding human Factor VIII:c or analogs thereof and/or by ligation of desired DNA sequences.

DNA sequences encoding human Factor VIII:c have been cloned. A cDNA encoding the full-length human protein as well as a cDNA encoding the deletion analog pDGR-2 have been deposited with the ATCC under accession numbers ATCC 39812 and 53100, respectively. Preparation and/or nucleotide sequence of a full-length human factor VIII:c cDNA has been set forth in detail in U.S. patent applications Ser. Nos. 546,650 (filed Oct. 28, 1983) and 644,086 (filed Aug. 24, 1984) and in International Patent Application No. PCT/US84/01641, published May 9, 1985 (Publn. No. WO 85/01961). A pSP64 recombinant clone containing the full-length human FVIII nucleotide sequence, designated as pSP64-VIII, is on deposit at the ATCC under Accession Number ATCC 39812.

Preparation and nucleotide sequence of a full-length human FV cDNA has been set forth in Jenny et al, supra. A recombinant clone containing a human FV nucleotide sequence, as depicted in Jenny et al, supra, has been designated pMT2-V and deposited at the ATCC under Accession No. ATCC 40515.

In order to simplify genetic manipulations, unique restriction sites have been engineered into FVIII and FV cDNAs by site-directed mutagenesis. Such techniques have also been used to modify a cDNA at specific sites, whether by replacing or deleting one or more bases. Such methods of mutagenesis include the M13 system of Zoller and Smith, Nucleic Acids Res. 10:6487–6500 (1982); Methods Enzymol. 100:468–500 (1983); and DNA 3:479–488 (1984), using single stranded DNA and the method of Morinaga et al., Bio/technology, 636–639 (July 1984), using heteroduplexed DNA. Exemplary oligonucleotides used in accordance with such methods are shown in Table I. It should be understood, of course, that all variant DNAs of this invention may be analogously produced by one skilled in the art by methods such as described herein for exemplary constructs.

The convenient exchange of domains between FVIII and FV was accomplished by introducing MluI sites into cDNAs encoding the respective factors. Because MluI does not cut within either of the cDNAs nor within the vector backbone, the unique introduced MluI sites facilitate the ability to exchange domains between the FVIII and FV cDNAs at will. Naturally, if such a site is present in alternative cDNAs or vectors such sites may be altered by site directed mutagenesis, if desired. Also, it should be understood that other unique restriction sites may be similarly introduced instead of MluI, or naturally occurring restriction sites may be abolished for the sake of convenience. In addition, since MluI recognizes the DNA sequence [5]'-ACGCGT-[3'], it will encode thr-arg. This allows one to introduce MluI sites at particular cleavage sites, e.g. thrombin-cleavage sites, in which the aminoterminal residue is arg, without drastically altering the conformation at that site so as to not interfere with biological activity. The particular MluI sites introduced to mediate a Bdomain exchange between factors V and VIII are at nucleotide positions in our FVIII cDNA corresponding to peptide positions 739-740 (changing the encoded sequence —PR— to —TR—) and at positions 1647-1648 (changing —QR— to —TR—) and in our FV cDNA at positions 708-709 (changing —IR— to —TR—) and at 1544-1545 (changing —LR— to —TR—). Partial restriction maps are as shown:

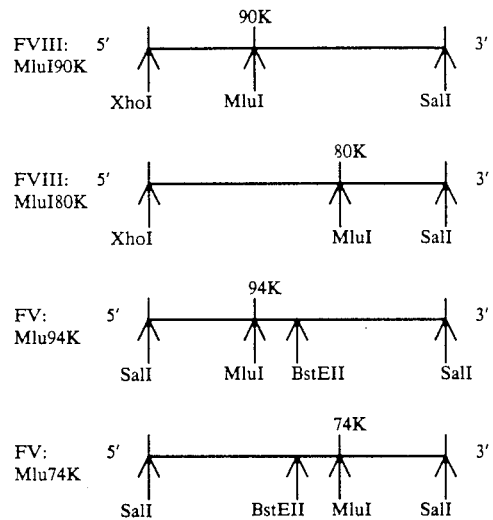

Thus, to construct the exemplary DNA encoding FVIII but with a FV B domain, we employed the following scheme. First, the FVIII MluI90K expression vectors was digested with MluI and SalI to excise the FVIII B domain and heavy chain-encoding region. The FVIII MluI80K expression vector was similarly digested and the light chain-encoding MluI-SalI fragment was isolated. The FV expression vectors MluI74K and MluI94K were digested with MluI and BstEII to excise the FV B domain encoding DNA in two pieces. The resultant DNAs were then ligated together as depicted below:

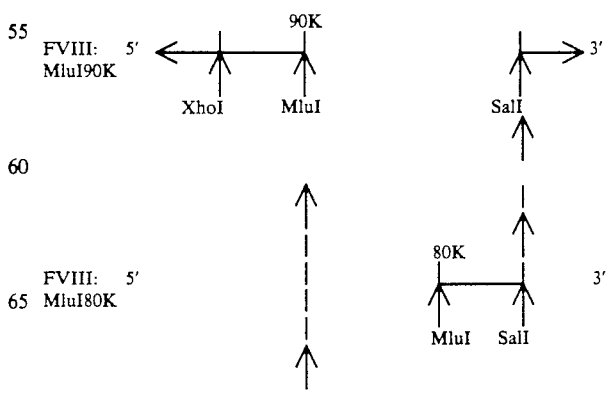

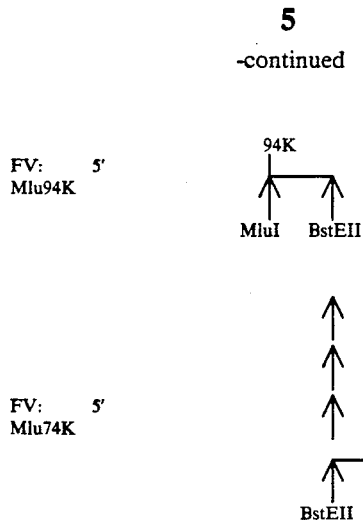

The resultant vector containing the FV B-domain-encoding region in the correct orientation within the FVIII-encoding sequence was identified and has been designated pMT2-VIIIB5. It should be noted that the —T(R)— codons at the 5' and 3' B-domain junctions may be engineered back to —P(R)— and —L(R)— codons, respectively, or to any other desired codons by conventional site-directed mutagenesis, if desired, or to preserve the reading frame.

It should also be understood that this process may be similarly conducted to exchange a region other than the B domain-encoding region, or a portion of a region, and may be repeated iteratively to effect multiple exchanges, and if desired, with intervening abolishing of MluI sites no longer useful. Alternatively, multiple (e.g. 4, 6, 8, etc.) MluI sites, for example, may be engineered into the starting vector to define multiple regions for exchange. In that case, the resultant vectors must be carefully analyzed to ensure that all exchanges have been properly effected without loss of any desired domain.

The B-domain exchange example illustrates one aspect of this invention, namely, the introduction of convenient restriction sites, such as MluI sites, at the junctions between different domains within DNAs encoding factors VIII and V, and the use of such DNAs in the construction of hybrid DNAs encoding FVIII-FV fusion proteins. It should be understood that there is some flexibility in the definition of domain boundaries. For example, the A1 domain of FVIII has its 3' boundary between amino acid residues 329 and 336. The 5' border of the A2 domain of FVIII is defined as being between residues 337 and 372. The 3' border of the FVIII A2 domain is defined as being between residues 698 and 740. The 5' border of the FVIII A3 domain is defined as between residues 1689 and 1721. Flexibility in the definition of domain boundaries has been previously discussed. See e.g. Vehar et al, supra: Kane & Davie, 1988, Blood 71:539; Jenny et al, supra. For convenience, the boundaries of the domains are frequently taken to be the sites of cleavage mediated by thrombin, activated protein C or Factor Xa. Of course, this invention also encompasses exchanging portions of one or more domains as well.

In the practice of certain specific embodiments of this invention, MluI sites may be engineered into FVIII and FV encoding DNAs at or within one or more of the following domain boundaries:

| Domain | AA residues at domain boundaries* | |
|---|---|---|
| | 5' Border | 3' Border |
| FVIII: | | |
| A1 | 1 | 329–336 |
| A2 | 372–377 | 711–740 |
| B | 740 | 1648 |
| A3 | 1689 | 2019 |
| C1 | 2020 | 2172 |
| C2 | 2173 | 2332 |
| Heavy chain acidic domain | 336 | 372 |
| Light chain acidic domain | 1649 | 1689 |
| FV: | | |
| A1 | 1 | 303–317 |
| A2 | 303–317 | 656–663 |
| B | 709 | 1545 |
| A3 | 1545 | 1877–1883 |
| C1 | 1877–1883 | 2036 |
| C2 | 2036 | 2196 |

*The amino acid number is given with respect to the mature FVIII or FV polypeptide Thus, as an example of another domain exchange, the FV A2 domain may be inserted in place of the FVIII A2 domain by expression of a hybrid DNA analogously prepared. For instance, MluI sites may be engineered into FVIII and FV expression vectors at the 5' and 3' borders of the A2 domains. The MluI fragments may then be excised from the vectors, and the FV A2-encoding region may be ligated into the FVIII expression vector from which the corresponding A2-encoding region had been excised, with or without retention of the FVIII heavy chain acidic region, depending on the location of the MluI site introduced into the FVIII cDNA.

Other examples of DNA exchange include inserting one or more FV DNA regions into the FVIII DNA in exchange for a non-corresponding region, e.g. replacing a FVIII Al domain with a FV A2 domain.

If the domain exchange process is conducted in vectors other than desired expression vectors, the new DNA sequences encoding the variants of this invention can be excised from the mutagenesis vectors and introduced into appropriate vectors for expression, preferably in mammalian cells. The procoagulant activity produced by the transiently transfected or stably transformed host cells may be measured by using standard assays for blood plasma samples.

TABLE I

| | | Exemplary Oligonucleotides | |
|---|---|---|---|
| Name | No. | Sequence | Mutation |
| | | [FVIII] | |
| FVIII 740 | 1. | 5'(GTA AAA ACA ATG CCA TTG AAA CGC GTA GCT TCT CCC AGA ATT C)3' | $P_{739}R_{740} \rightarrow T_{739}R_{740}$ |
| Screen 740 | 2. | 5'(TTG AAA CGC GTA GCT)3' | *(1) |

TABLE I-continued
Exemplary Oligonucleotides

| Name | No. | Sequence | Mutation |
|---|---|---|---|
| FVIII 1648 | 3. | 5'(CCA GTC TTG AAA CGC CAT ACG CGT GAA ATA ACT CGT ACT ACT C)3' | $Q_{1647}R_{1648} \rightarrow T_{1647}R_{1648}$ |
| Screen 1648 | 4. | 5'(GCC ATA CGC GTG AAA)3' | *(3) |
| FVIII 1689 | 5. | 5'(GAG GAT GAA AAT CAG AGC ACG CGT AGC TTT CAA AAG AAA ACA CG)3' | $P_{1688}R_{1689} \rightarrow T_{1688}R_{1689}$ |
|  | 6. | 5'(AGA GCA CGC GTA GCT)3' | *(5) |
| FVIII 372 | 7. | 5'(GCT TCC TTT ATC AA ACG CGT TCA GTT GCC AAG AAG CAT CC) | $I_{371}R_{372} \rightarrow T_{371}R_{372}$ |
| Screen 372 | 8. | 5'(CCA AAC GCG TTC AGT)3' | *(7) |
| FVIII 226 | 9. | 5'(G GAT AGG GAT GCT GCA TCT ACG CGT GCC TGG CCT AAA ATG CAC)3' | $A_{225}R_{226} \rightarrow T_{225}R_{226}$ |
| Screen 226 | 10. | 5'(ATC TAC GCG TGC CTG)3' | *(9) |
| FVIII 336 | 11. | 5'(GTC CAG AGG AAC CCC AA ACG CGT ATG AAA AAT AAT GAA G)3' | $L_{335}R_{336} \rightarrow T_{335}R_{336}$ |
| Screen 336 | 12. | 5'(CCA AAC GCG TAT GAA)3' | *(11) |
| FVIII 562 | 13. | 5'(CAA AGA ATC TGT AGA T ACG CGT GGA AAC CAG ATA ATG TC)3' | $Q_{561}R_{562} \rightarrow T_{561}R_{562}$ |
| Screen 562 | 14. | 5'(GTA GAT ACG CGT GGA)3' | *(13) |
| FVIII 698 | 15. | 5'(GGG TGC CAC AAC TCA GAC ACG CGT AAC AGA GGC ATG ACC G)3' | $F_{697}R_{698} \rightarrow T_{697}R_{698}$ |
| Screen 698 | 16. | 5'(TCA GAC ACG CGT AAC)3' | *(15) |
| FVIII 700 | 17. | 5'(GC CAC AAC TCA GAC TTT CGG ACG CGT GGC ATG ACC GCC TAA CTG)3' | $N_{699}R_{700} \rightarrow T_{699}R_{700}$ |
| Screen 700 | 18. | 5'(TTT CGG ACG CGT GGC)3' | *(17) |
| FVIII 1313 | 19. | 5'(GTC ACG CAA CGT AGT ACG CGT GCT TTG AAA CAA TTC)3' | $K_{1312}R_{1313} \rightarrow T_{1312}R_{1313}$ |
| Screen 1313 | 20. | 5'(CGT AGT ACG CGT GCT)3' | *(19) |
| FVIII 1721 | 21. | 5'(CC CCA CAT GTT CTA AGA ACG CGT GCT CAG AGT GGC AGT G)3' | $N_{1720}R_{1721}-T_{1720}R_{1721}$ |
| Screen 1721 | 22. | 5'(TAA GAA CGC GTG CTC)3' | *(21) |
| FVIII 2020 | 23. | 5'(GCA CAC TTT TTC TGG TGT AC AGC ACG CGT TGT CAG ACT CCC CTG GG)3' | $N_{2019}K_{2020} \rightarrow T_{2019}R_{2020}$ |
| Screen 2020 | 24. | 5'(ACA GCA CGC GTT GTC)3' | *(23) |
| FVIII 2173 | 25. | 5'(GGG CTG TGA TTT A ACG CGT TGC AGC ATG CCA TTG GG)3' | $N_{2172}S_{2173}-T_{2172}T_{2173}$ |

TABLE I-continued
Exemplary Oligonucleotides

| Name | No. | Sequence | Mutation |
|---|---|---|---|
| Screen 2173 | 26. | 5'(GAT TTA ACG CGT TGC)3' | *(25) |
| | | [FACTOR V] | |
| FV 709 | 27. | 5'(GGC TGC AGC ATT AGG A<u>AC</u> <u>GCG</u> <u>T</u>TC ATT CCG AAA CTC ATC ATT G)3' | $I_{708}R_{709}$-$T_{708}R_{709}$ |
| Scn 709 | 28. | 5'(AGG AAC GCG TTC ATT)3' | *(27) |
| FV 1545 | 29. | 5'(CAT TGC AGC ATG GTA C<u>AC</u> <u>GCG</u> <u>T</u>AG CAA CAA TGG AAA CAG AAG)3' | $L_{1544}R_{1545}$-$T_{1544}R_{1545}$ |
| Scn 1545 | 30. | 5'(TAC ACG CGT AGC AA)3' | *(29) |
| FV 348 | 31. | CCA GCG AAT ATG GAC AAA AAA <u>ACG</u> <u>CGT</u> TCT CAG CAT TTG GAT AAT TTC | $Y_{347}R_{348} \longrightarrow T_{347}R_{348}$ |
| Scn 348 | 32. | AA AAA ACG CGT TCT CAG | *(31) |
| FV 506 | 33. | GTA AGA GCA GAT CCC TGG AC<u>A</u> <u>CGC</u> <u>GT</u>G AAA TAC AGA GGG CAG CAG | $R_{505}R_{506} \longrightarrow T_{505}R_{506}$ |
| Scn 506 | 34. | GGA CAC GCG TGG AAT | *(33) |
| FV 505 | 35. | CTG TAA GAG CAG ATC CCT G<u>AC</u> <u>GCG</u> <u>T</u>CG AGG AAT ACA GAG GGC AGC | $D_{504}R_{505} \longrightarrow TR$ |
| Scn 505 | 36. | CCT GAC GCG TCG AG | *(35) |
| FV 1018 | 37. | CAC ACC ATG CTC CTT TAT CT<u>A</u> <u>CGC</u> <u>GT</u>A CCT TTC ACC CTC TAA GAA GTG | $P_{1017}R_{1018} \longrightarrow TR$ |
| SCn 1018 | 38. | TAT CTA CGC GTA CCT | *(37) |
| FV 1765 | 39. | GAA AAG AAG TCC CGA AGT TCT <u>ACG</u> <u>CGT</u> CTC ACA TCC TCA GAA ATG | $W_{1764}R_{1765} \longrightarrow TR$ |
| ScN 1765 | 40. | T TCT ACG CGT CTC AC | *(39) |
| FV 313 | 41. | CCA GGA ATC TTA AGA AAA TA<u>A</u> <u>CGC</u> <u>GT</u>G AGC AGA GGC GGC ACA TGA AG | $T_{312}R_{313} \longrightarrow TR$ |
| Scn 313 | 42. | G AAA ATA ACG CGT GAGC | *(41) |
| FV 643 | 43. | GTT AAC TTC CAT GAA TTC TAG T<u>AC</u> <u>GCG</u> <u>T</u>AG CAA AAA GCT GAG GCT G | $P_{642}R_{643} \longrightarrow TR$ |
| Scn 643 | 4. | CTAGTACGCGTAGCA | *(43) |
| FV 1878 | 45. | CCA TTT CTT ATC ATG GAC <u>ACG</u> <u>CGT</u> TGT AGG ATG CCA ATG GGA C | $R_{1877}D_{1878} \longrightarrow TR$ |
| Scn 1878 | 46. | GGACACGCGTTGTAG | *(45) |
| FV 2037 | 47. | GAA CTG CAA GGT TGT GAG GTA <u>ACG</u> <u>CGT</u> TGT TCC ACA CCC CTG GGT ATG | $N_{2036}G_{2037} \longrightarrow TR$ |

TABLE I-continued

| Name | No. | Exemplary Oligonucleotides Sequence | Mutation |
|---|---|---|---|
| Scn 2037 | 48. | GGTAACGCGTTGTTC | *(47) |

*Used for screening mutagenesis event effected with the oligonucleotide indicated in parentheses. Codons for replacement amino acids are underlined. As those skilled in this art will appreciate, oligonucleotides can be readily constructed for use in deleting one or more amino acids or for inserting a different (replacement) amino acid at a desired site by deleting one or more codons or substituting the codon for the desired amino acid in the oligonucleotide, respectively. Other mutagenesis oligonucleotides can be designed based on an approximately 20–50 nucleotide sequence spanning the desired site, with replacement or deletion of the original codon(s) one wishes to change.

The eukaryotic cell expression vectors described herein may be synthesized by techniques well known to those skilled in this art. The components of the vectors such as the bacterial replicons, selection genes, enhancers, promoters, and the like may be obtained from natural sources or synthesized by known procedures. See Kaufman et al., *J. Mol. Biol.*, 159:601–621 (1982); Kaufman, *Proc Natl. Acad. Sci.* 82:689–693 (1985). Eucaryotic expression vectors useful in producing variants of this invention may also contain inducible promoters or comprise inducible expression systems as are known in the art.

Established cell lines, including transformed cell lines, are suitable as hosts. Normal diploid cells, cell strains derived from in vitro culture of primary tissue, as well as primary explants (including relatively undifferentiated cells such as haematopoetic stem cells) are also suitable. Candidate cells need not be genotypically deficient in the selection gene so long as the selection gene is dominantly acting.

The host cells preferably will be established mammalian cell lines. For stable integration of the vector DNA into chromosmal DNA, and for subsequent amplification of the integrated vector DNA, both by conventional methods, CHO (Chinese Hamster Ovary) cells are presently preferred. Alternatively, the vector DNA may include all or part of the bovine papilloma virus genome (Lusky et al., *Cell*, 36: 391–401 (1984) and be carried in cell lines such as C127 mouse cells as a stable episomal element. Other usable mammalian cell lines include HeLa, COS-1 monkey cells, melanoma cell lines such as Bowes cells, mouse L-929 cells, 3T3 lines derived from Swiss, Balb-c or NIH mice, BHK or HaK hamster cell lines and the like.

Whichever type of expression vector is used, it may be preferable to co-express the variant FVIII DNA with a DNA sequence encoding vWF or an analog thereof, e.g. as described in WO 87/06101 and WO 88/08035. It may also be preferred to express the protein in media containing a protease inhibitor such as aprotinin e.g. in an amount from about ~0.01-~5%, preferably 0.5-1.0%, (vol/vol) (Aprot., 15-30 Trypsin inhibitor units(TIU)/ml, Sigma) or corresponding amounts of activity units of other protease inhibitors.

Stable transformants then are screened for expression of the procoagulant product by standard immunological or activity assays. The presence of the DNA encoding the procoagulant proteins may be detected by standard procedures such as Southern blotting. Transient expression of the procoagulant genes during the several days after introduction of the expression vector DNA into suitable host cells such as COS-1 monkey cells is measured without selection by activity or immunologic assay of the proteins in the culture medium.

Following the expression of the variant DNA by conventional means, the protein so produced may be recovered, purified, and/or characterized with respect to physiochemical, biochemical and/or clinical parameters, all by known methods.

The proteins of this invention should bind to appropriate monoclonal antibodies directed to human Factor VIII:C or FV (i.e., where the epitope recognized is present in the desired protein) and may thus be recovered and/or purified by immunoaffinity chromatography using such antibodies and/or by conventional FVIII purification methods. Furthermore, these compounds should possess procoagulant activity.

The proteins produced in accordance with this invention can be formulated into pharamaceutically acceptable preparations with a parenterally acceptable vehicle and/or one or more excipients in accordance with procedures known in the art.

The pharmaceutical preparations of this invention, suitable for parenteral administration, may conveniently comprise a sterile lyophilized preparation of the protein which may be reconstituted by addition of sterile solution to produce solutions preferably isotonic with the blood of the recipient. The preparation may be presented in unit or multi-dose containers, e.g. in sealed ampoules or vials. Their use would be analogous to that of human factor VIII (or FV in certain cases where one or more FV A and/or C domains are present), appropriately adjusted for potency.

The invention will be further understood with reference to the following illustrative experimental examples and procedures, which are purely exemplary, and should not be taken as limiting the true scope of the present invention, as described in the claims.

PLASMID DERIVATIONS

A. FVIII

The mutagenesis of factor VIII cDNAs was performed directly in the expression plasmid in order to minimize inconvenience in shuffling sequences between different vectors. Generally, the approach taken for mutagenesis was derived from the procedure of Morinaga with modifications. This approach is facilitated by the construction of plasmids which have convenient unique restriction sites in the factor VIII expression plasmid. The following depicts the construction of a factor VIII expression plasmid which has unique Eco RV, HpaI, Cla I and Xba I restriction sites. Plasmid pMT2 may be obtained by EcoRI digestion of pMT2-VWF, which has been deposited with the American Type Culture Collection under accession number ATCC 67122. EcoRI digestion excises the cDNA insert present in pMT2-VWF, yielding pMT2 in linear form which can be ligated and used to transform *E. coli* HB 101 or DH-5 to ampicillin resistance. Plasmid pMT2 DNA can be prepared by conventional methods. pMT2VIII was then constructed by digesting pMT2 with Eco RV and XbaI, treating the digested DNA with Klenow fragment of DNA polymerase I, and ligating Cla linkers (NEBiolabs, CATCGATG). This removes bases 2171 to 2421 starting from the Hind III site near the SV40 origin of replication and enhancer sequences of pMT2 (the ClaI derivative of pMT2). The factor VIII cDNA was excised from pSP64 VIII with SalI and blunted with T4 DNA polymerase, and EcoRI adapters were added (AATTCCTCGAGAGCT). The EcoRI-adapted factor VIII cDNA was then ligated into the EcoRI site of the ClaI derivative of pMT2. The resultant plasmid is called pMT2-VIII.

B. FV

The mutagenesis of FV cDNAs was performed both in the expression vector and in a cloning shuttle vector. The mutagenesis approach was derived from Morinaga, supra, with modifications.

The expression vector used for FV expression was also a pMT2 derivative. Plasmid pMT2 DNA was obtained in linear form as previously described from pMT2-VWF (ATCC 67122). The EcoRI site was then modified by ligation to an adapter containing a SalI site (see below). The ClaI derivative of pMT2 was then constructed by digestion with EcoRV and XbaI, treating the digested DNA with Klenow fragment of DNA polymerase I, and ligating ClaI linkers (N. E. Biolabs, CATCGATG). This removes bases 2267-2421, numbering in a clockwise manner from the HindIII site on the early side of the pMT2 SV40 origin of replication and enhancer sequences.

The FV cDNA was assembled from two overlapping Charon 21Aλ recombinants, λV401 and λVI, each containing portions of FV cDNA derived from an oligo (dT)-primed human fetal liver cDNA library (See Jenny et al, supra).

The following strategy was used to assemble the full-length cDNA and remove flanking DNA sequences. The λV401 clone was digested with SacII to remove the FV cDNA, which was ligated to SacII linearized Bluescript KS (+) cloning vector (Stratagene), resulting in the plasmic 401B5-6. λDNA sequences were removed from 401B5-6 by digestion with HhaI (nucleotide 41 in the FV cDNA), treatment with Klenow fragment of DNA polymerase I, and then digestion with BglII (nucleotide 4275 in the FV cDNA). This resulted in a 4234 bp blunted BglII fragment free of flanking λ sequences. This 4234 bp fragment was inserted by ligation into the EcoRV and Bam HI cloning sites of Bluescript KS (+), generating plasmid Blu401.

The FV cDNA in the λVl clone was removed by SacII digestion of λVl. This SacII fragment was then ligated to the linearized SacII Bluescript KS (+) cloning vector, resulting in the plasmid VIBS10. VIBS10 was then digested with HpaI (nucleotide 6854 in the FV cDNA) and ligated to the following EcoRI modified adapters:

```
5'  AATTCCGTCGACTCTAGAG  3'
3'        GGCAGCTGAGATCTC  5'
``` resulting in plasmid BluV1-RI.

Three restriction sites were important in the construction of the expression vector containing the full-length FV cDNA. A SalI site in the polylinker cloning region of Bluescript KS (+) provides a unique SalI site which is 5' of the FV cDNA sequences. There is also a unique BstEII site in the FV cDNA (nucleotide 3666) present in both plasmids Blu401 and BluV1-R1. A unique SalI site results from the addition of the EcoRI modified adapters introduced into the 3' end of the Blu V1-R1.

The recombinant Blu40l will contribute the 5' end sequences of the FV cDNA, while the Blu V1-RI comprises the 3' end of the intact cDNA. Three restriction fragments from the pMT2 derivative, Blu40l and Blu V1-R1 were purified after electrophoresis on a 1% low-melting temperature agarose gel in tris-acetate. The isolation of the 3625 bp SalI-BstEII fragment was facilitated by also digesting with XMNI to remove a contaminating, co-migrating fragment. The pMT2 expression vector wa linearized with SalI digestion and then treated with calf-intestine phosphatase. The three fragments: (i) the 3625 bp SalI/BstEII Blu 401 fragment, (ii) the 3188 bp SalI/BstEII Blu V1-R1 fragment, and (iii) SalI digested pMT2 were ligated to generate the expression plasmid pMT2-V, which has been deposited with the American Type Culture Collection under Accession No 40515.

A second plasmid containing the full-length FV cDNA was constructed in Bluescript KS (+). Blu40l was digested with SacII (3' site in Bluescript cloning polylinker) and BstEII (nucleotide 3666 in the FV cDNA). This fragment containing the Bluescript vector sequences and the 3625 bp fragment of FV sequences starting at the 5' end of the FV cDNA to the BstEII site was isolated. Blu V1-RI DNA was digested with BstEII (nucleotide 3666) and SalI (3' of the EcoRI modified adapter), to release a fragment of approximately 3900 bp and which contains the 3' end of the FV cDNA sequences. The exact size of this fragment is unclear because is still contains λ DNa sequences. The BstEII/-SacII Blu40l and BstEII/SacII Blu V1-RI were ligated together to produce the plasmid BluV.

λ DNA sequences were removed by SalI digestion of BluV and the intact full-length FV cDNA (6813 bp) contained on the SalI fragment was isolated. Bluescript KS (+) was linearized by SalI digestion and treated with calf-intestine alkaline phosphatase and ligated to the SalI fragment containing the full-length FV cDNA. The resultant plasmid, designated BluKSVΔλ, contains the full-length FV cDNA devoid of any λ sequences.

MUTAGENESIS (1) The mutagenesis was performed with the following DNA preparations. Plasmid pMT2-VIII was linearized with ClaI, treated with calf intestinal phosphatase, and separated on a low melting temperature tris-acetate agarose gel. The band of linearized DNA was then extracted by absorption to silica dioxide and eluted in tris-EDTA, or by phenol extraction and ethanol precipitation. A second lot of pMT2-VIII was digested with KpnI-XhoI, KpnI-EcoRV or EcoRV-XbaI and the DNA fragments were separated by electrophoresis on a low melting temperature agarose gel and extracted as above. Plasmid pMT2-V was linearized with NheI, treated with calf intestinal phosphatase, and separated by electrophoresis on a low melting temperature tris-acetate agarose gel. The linearized DNA band was extracted with phenol and precipitated in ethanol. The DNA pellet was resuspended in trisEDTA. A second lot of pMT2-V was digested with ApaI and DraII, the DNA fragments were separated on low melting temperature agarose gel and extracted as described above. Plasmid BluKSV was linearized with SacII, treated with calf intestinal phosphatase and the DNA was separated by electorphoresis on low melting temperature agarose gel. A second lot of BluKSV was digested with EcoRV and SphI and was separated in the same manner. The DNA fragments were extracted with phenol as described.

(2) One ug of each of the appropriate plasmids were mixed and the volume was adjusted to 18 ul and 2.0 ul of 2 N NaOH was added.

(3) The mixture was denatured at room temperature for 10 min, then neutralized with 180 ul of a solution which is 0.02 N HCl and 0.1 M Tris-HCl pH 8.0.

(4) 20 picomoles of phosphorylated mutagenic oligonucleotide was added to 40 ul of the heteroduplex mixture.

(5) The mixture was placed in a 68° C. heat block for 90 min. After the incubation the mixture was allowed to slowly cool at room temperature.

(6) For each mutagenic reaction, 40 ul of the heteroduplex oligo-nucleotide mixture was used. The reactions were made 2 mM MgCl₂, 1 mM β-mercaptoethanol, 400 uM ATP, 100 uM deoxynucleotide triphosphate, 3–4 units/ul of Klenow fragment of $E.$ $coli$ DNA polymerase I and 400 units/ul of T4 DNA ligase.

(7) The reactions were incubated for 10 minutes at room temperature, transferred to 16° C. and incubated overnight.

(8) The reaction was terminated by phenol-chloroform extraction and ethanol precipitation, and the resultant pellet was washed with 70% ethanol and resuspended in 10 ul of sterile $H_2O$.

(9) DNA was then used to transform competent HB101 or DH-5 bacteria. The ampicillin resistant colonies were screened with $1 \times 10^6$ cpm/ml of a $^{32}P$-labeled screening oligonucleotide in 5×SSC, 0.1% SDS, 5×denhardt's reagent, and 100 ug/ml denatured salmon sperm DNA.

(10) The filters were washed with 5x SSC, 0.1% SDS at a temperature 5 degrees below the calculated melting temperature of the oligonucleotide probe.

(11) DNA was prepared from positively hybridizing clones and analyzed initially by digestion with different restriction enzymes and agarose gel electrophoresis. DNA was transferred to nitrocellulose and filters were prepared and hybridized to the screening probes in order to ensure the mutagenic oligonucleotide was introduced into the correct fragment.

(12) DNA was then retransformed into $E.$ $coli$ and ampicillin resistant colonies were screened for hybridization to the screening oligonucleotide.

(13) Final mutations were confirmed by DNA sequencing (e.g., Sanger et al., 1977, Proc. Natl. Acad. Sci. USA 74:5463–5467).

Experimental Strategy and Assay Methods

The activity of FVIII-FV hybrid proteins was analyzed by transient expression of the proteins by COS-1 monkey kidney cells transfected with the hybrid DNAs of this invention. Plasmid DNAs were prepared by banding DNA in CsCl and used to transfect COS-1 cells as described (Kaufman, 1985, Proc Natl Acad Sci USA :689). At 60 hr post transfection, conditioned media were taken for FVIII or FV activity assay. FVIII is assayed by the Kabi coatest chromogenic assay method (Kabi) or the ability to clot FVIII-deficient plasma (activated partial thromboplastin time, APTT) before and after thrombin activation. FV is assayed by the ability to clot FV-deficient plasma before and after thrombin activation (APTT). To analyze the synthesis and secretion of the mutant molecules, and to ensure that introduction of the MluI restriction sites (Thr-Arg) do not alter cleavage at any mutagenized cleavage sites, the transfected cells were labeled with $^{35}S$-methionine for 6 hrs at 60 hr post-transfection, and the conditioned media and cell extracts were prepared and analyzed by immunoprecipitation with anti-FVIII or FV-specific antibodies and electrophoresis of the precipitates on SDS-polyacrylamide gels.

EXAMPLES

Example 1

Alteration of the 90 kDa FVIII cleavage site

Mutagenesis of the 90 kDa cleavage site in Factor VIII was performed by the gapped heteroduplex method as described (Morinaga et al, Biotechnology 84:636–639) using the Kpn-EcoRV 10.1 kb fragment from pMT2-VIII and the ClaI linearized pMT2-VIII DNA to produce gapped heteroduplexes. The mutagenic oligonucleotide was No. 1 in Table I and the screening oligonucleotide was the 15-mer No. 2 in Table I. The resultant mutant was verified to be correct by DNA sequencing (Sanger et al 1977 PNAS 74: 5463). The resultant DNA (MluI90K) was prepared by banding to equilibrium in CsCl and transfected into COS-1 cells as described above. Analysis of $^{35}S$-methionine labeled cell extracts and conditioned medium by immunoprecipitation and gel electrophoresis showed that the factor VIII synthesized was similar in size and amount to wildtype factor VIII and was cleaved appropriately by thrombin. The mutation had no effect on factor VIII activity as measured by the Kabi-coatest activity assay (Table II).

Example II

Alteration of the 80 kDa factor VIII cleavage site

Mutagenesis of the 80 kDa cleavage site was performed by preparing a gapped heteroduplex using ClaI linearized pMT2-VIII DNA and the EcoRV-XbaI 9.2 kb fragment of pMT2-VIII. The mutagenic oligonucleotide was No. 3 in Table I and the screening oligonucleotide was No. 4 in Table I. The resultant mutant was verified to be correct by DNA sequencing as above. The resultant DNA (MluI80K) was prepared and transfected into COS-1 cells as described above. Analysis of secreted factor VIII activity by the Kabi-coatest method and analysis of $^{35}S$-methionine labeled cell extracts and conditioned medium by immunopreoipitation and gel electrophoresis demonstrated the factor VIII was appropriately secreted, cleaved by thrombin, and not altered in its cofactor activity (Table II).

Example III

Mutagenesis of the 73 kDa cleavage site in factor VIII

The mutagenesis was performed with the heteroduplex described in Example II utilizing the 44-mer oligonucleotide No. 5 in Table I and the screening oligonucleotide No. 6, Table I. The resultant DNA (MluI73k) was verified to be correct by DNA sequencing. The resultant DNA was transfected into COS 1 cells as described above. The protein synthesized was similar to wildtype factor VIII in both factor VIII activity and expression level (Table II).

Example IV

Mutagenesis of the 94 kDa factor V cleavage site

Mutagenesis of the 94 kDa cleavage site of factor V was performed using a gapped heteroduplex prepared with the NheI/ApaI 10.2 kb fragment of pMT2V and DraII 11.8 kb linearized pMT2V. The mutagenic oligonucleotide was a 43-mer No. 27 Table I and the 15 mer screening oligonucleotide No. 28, Table I. The resultant DNA (MluI94K) was confirmed to be correct by DNA sequencing and was transfected into COS-1 cells as described above. The resultant secreted protein was similar in amount to wildtype factor V, as determined by factor V clotting assays before and after thrombin activation and by analysis of the synthesis and secretion of factor V by $^{35}$S-methionine labeling of cells and analysis of cell extracts and conditioned medium by SDS-polyacrylamide gel electrophoresis of immuno-precipitated factor V.

Example V

Mutagenesis of the 74 kDa factor V cleavage site

Mutagenesis was performed as described above by preparing gapped heteroduplexes with the Eco RV-SphI 9.0 kb fragment of BluKSVΔλ and SacI 9.8 kb linearized BluKSVΔλ and using the mutagenic oligonucleotide (No. 29, Table I) and the 15-mer screening oligonucleotide (No. 30, Table I). The resultant DNA (MluI74K) was confirmed to be correct by DNA sequencing.

Example VI

Preparation of DNA encoding factor VIII with a factor V B domain

A hybrid factor VIII/factor V was assembled utilizing the following approach. The factor VIII expression plasmid MluI90K was digested with SalI and MluI and the large 7.2 kb fragment was isolated by electrophoresis on a low melting temperature agarose gel. The factor VIII expression plasmid MluI80K was digested with MluI and SalI and the small 2.3 kb fragment was isolated by electrophoresis on a low melting temperature gel. The factor V B domain was assembled from two fragments: (1) plasmid MluI74K was digested with MluI and BstEII to yield a 1.1 kb 3' end of the factor V B domain, and (2) plasmid MluI94K was directed with MluI and BstEII to yield a 1.4 kb 5' end of the factor V B domain. These fragments were isolated after electrophoresis on a low melting temperature agarose gel.

The hybrid was assembled by a 4-way ligation of the above fragments in low melting agarose. The hybrid was verified to be properly assembled by extensive restriction endonuclease digestion and gel electrophoresis analysis and by sequencing across the factor V-factor VIII junctions. The resultant DNA, pMT2-VIIIB5, was transfected into COS-1 cells and analyzed as described below.

Factor VIII activity was measured by the Kabi-coatest assay method (Table II). In control experiments, wildtype factor VIII is expressed and secreted as a two chain molecule. Factor V is secreted as a single chain polypeptide and is expressed at a 10-20- fold greater level than factor VIII. The hybrid exhibited 2-4 fold higher activity than the wildtype factor VIII protein. This was a consequence of more efficient secretion from the cell. Analysis of the $^{35}$S-methionine labeled conditioned medium revealed that the hybrid protein was secreted as a single chain polypeptide which migrates with an apparent molecular weight (approximately 300 kDa) slightly less than factor V. The appropriate cleavage products were obtained by thrombin digestion prior to electrophoresis. In addition, the hybrid was immunoprecipitated by a monoclonal antibody specific to the heavy chain of factor VIII and by a monoclonal antibody specific to the B-domain of factor V, suggesting that the protein is properly folded.

Example VII

Replacement of the factor VIII light chain with the factor V light chain

Plasmid MluI90K is digested with SalI and Eco RV and the 8.9 kb factor VIII heavy chain encoding fragment isolated. The factor VIII B domain is isolated from MluI80K or MluI73K by digestion with MluI and EcoRV and the fragments of 1778 and 1054 bp, respectively, are isolated The 2.0 kb MluI-SalI factor V light chain encoding fragment is isolated from MluI74K. The fragments are assembled with a 3-way ligation by standard techniques. This will yield a hybrid that contains the acidic region of the light chain of factor VIII if one uses the 1178 bp fragment or a hybrid that lacks the acidic region by using the 1054 bp fragment.

Example VIII

Replacement of the heavy chain of fVIII with the f V heavy chain

The 8.3 kb XhoI-EcoRV fragment encoding the light chain of factor VIII is isolated from MluI80K, the 1.7 kb MluI-EcoRV fragment encoding the factor VIII B domain is isolated from MluI90K, and the 2.3 kb SalI-MluI factor V heavy chain encoding fragment is isolated from MluI90K. These are ligated together in a 3-way ligation and screened for the appropriate clone by colony hybridization to specific oligonucleotides that hybridize to the three fragments.

| | Factor VIII Activity | | |
|---|---|---|---|
| | Exp1 mu/ml | Exp2 mu/ml | Exp3 mu/ml |
| pMT2-V | — | — | — |
| pMT2-VIII | 52 | 40 | 218 |
| pMT2-VIIIB5 | 111 | 79 | 428 |
| MluI90K | ND | 30 | ND |
| MluI80K | ND | 30 | ND |
| MluI73K | ND | 35 | ND |

(ND = not determined)

Example IX

Replacing the FVIII light chain with the FV light chain

Plasmid MluI73K is digested with MluI and SalI to excise the FVIII light chain encoding fragment. Plasmid MluI74K is digested with MluI and SalI to excise the FV light chain, which is then isolated and ligated to the MluI/SalI-digested MluI73K plasmid DNA. The resultant plasmid encodes a hybrid protein comprising the FVIII heavy chain, FVIII B domain, FVIII acidic regions and the FV light chain.

Example X

Replacing the FVIII light chain and B domain with corresponding elements from FV A set of overlapping synthetic oliognucleotides are prepared, kinased and ligated to produce the following synthetic DNA:

```
CGCGTGAAATAACTCGTACTACTCTTCAGTCAGATCAAGAGGAAATTGACTATGAT
     ACTTTATTGAGCATGATGAGAAGTCAGTCTAGTTCTCCTTTAACTGATACTA

GATACCATATCAGTTGAAATGAAGAAGGAAGATTTTGACATTTATGATGAGGATGAA
     CTATGGTATAGTCAACTTTACTTCTTCCTTCTAAAACTGTAAATACTACTCCTACTT

AATCAGAGCA
TTAGTCTCGTGCGC
```

That synthetic DNA represents a MluI cassette encoding the acidic region present between the 80 and 73 kD cleavage sites of FVIII. Alternatively, MluI sites may be introduced into the FVIII expression vector at the 80 and 73 kD sites using oligonucleotides #3 and #5 from Table I, as separately described in Examples II and III. The corresponding cassette may then simply be excised from the vector with MluI. The cassette is then ligated to the MluI/BstEII fragment isolated from MluI74K in Example VI, and the resulting MluI fragment containing the FVIII acidic regionencoding fragment ligated in the correct orientation to the partial FV B domain-encoding fragment is isolated. That fragment is then ligated by the procedure of Example VI to the SalI/MluI fragment of MluI90K, the MluI/BstEII fragment of MluI94K (both obtained as in Example VI), and to the MluI/SalI fragment of MluI74K encoding the FV light chain. The hybrid is verified to be properly assembled as in Example VI. The resultant DNA, pMT2-VIIIB5/LC5 encodes a hybrid protein comprising, in N-terminal to C-terminal order, the FVIII heavy chain with its acidic region, the FV B domain, the acidic region from the FVIII light chain, and the FV light chain.

Example XI

Deleting the FVIII B domain and replacing the light chain with the FV light chain Example X is repeated with the following modifications. The MluI cassette encoding the FVIII light chain acidic region is ligated directly to the MluI/SalI digested MluI90K FVIII plasmid and the MluI/SalI fragment of MluI74K which encodes the FV light chain. The properly assembled hybrid cDNA encodes a protein comprising the FVIII heavy chain linked to the FV light chain by the acidic region derived from the FVIII light chain.

Example XIIcI Replacing the A2, B, A3, C1 and C2 FVIII domains

A. The MluI cassette encoding the FVIII light chain acidic region is ligated to the BstEII/MluI FV fragment encoding the C-terminal part of the FV B domain. The correctly oriented BstEII/MluI reaction product encoding the C-terminal part of the FV B domain linked to the FVIII light chain acidic region thus obtained is ligated to the MluI/SalI fragment from MluI74 which encodes the FV light chain. The correctly oriented BstEII/SalI fragment (fragment "A") is identified and gel purified.

B. A FV vector is prepared with a MluI site introduced just 5' of the region encoding the A2 domain at peptide positions 312–313 using oligonucleotide #41. The MluI/BstEII fragment encoding the FV A2 and part of the FV B domain is excised therefrom and gel purified (fragment "B").

C. A FVIII vector is prepared with a MluI site introduced just 5' to the FVIII A2 region at peptide position 372 using oligonucleotide #7. That vector is then digested with MluI and SalI to excise most of the FVIII coding region leaving only the A1 and heavy chain acidic region. The larger MluI/SalI fragment is then gel purified and ligated to fragments A and B. The correctly oriented resulting vector contains the following coding region:

```
 ┌─────┬─────┐    B     ┌─────┬─────┬─────┐
 │ A-1 │ A-2 ├──────────┤ A-3 │ C-1 │ C-2 │
 └─────┴─────┘          └─────┴─────┴─────┘
        |<──── FV ────>|    |<──── FV ────>|
 |<───>|                    | |
  FVIII ↑                    ↑ FVIII
        |                    |
```

We claim:

1. A DNA encoding a procoagulant-active protein characterized by a peptide sequence of human Factor VIII except within the B domain where it is characterized by peptide sequence of human Factor V.

2. An expression vector containing a DNA of claim 1.

3. A host cell containing and capable of expressing a DNA of claim 1.

4. A method for producing a procoagulant protein which comprises:
   (a) producing a host cell containing and capable of expressing a DNA of claim 1;
   (b) culturing the host cell under suitable conditions permitting expression of the DNA; and,
   (c) recovering the protein so produced from the cell culture.

5. A procoagulant protein encoded by the DNA of claim 1.

* * * * *